United States Patent [19]

Hellerbach et al.

[11] 3,954,838

[45] May 4, 1976

[54] PROCESS FOR PREPARING ALKYL (N-PHENYLSULFONYLOXY) CARBAMATES

[75] Inventors: Joseph Hellerbach, Basel, Switzerland; Armin Walser, West Caldwell, N.J.; Hermann Bretschneider, Innsbruck, Austria; Werner Rudolph, Lorrach, Germany

[73] Assignee: Hoffmann-La Roche Inc., Nutley, N.J.

[22] Filed: Aug. 29, 1974

[21] Appl. No.: 501,585

Related U.S. Application Data

[62] Division of Ser. No. 373,070, June 25, 1973, Pat. No. 3,853,953, which is a division of Ser. No. 111,731, Feb. 1, 1971, Pat. No. 3,772,271.

[30] Foreign Application Priority Data

Feb. 11, 1970 Switzerland............... 111731/70

[52] U.S. Cl. ........................ 260/471 C; 260/470; 260/481 C; 260/482 C; 260/562 N; 260/239.3 D; 424/244

[51] Int. Cl.² ................................ C07D 125/06
[58] Field of Search .............. 260/239.3 D, 471 C

[56] References Cited

UNITED STATES PATENTS

| | | | |
|---|---|---|---|
| 3,772,271 | 11/1973 | Hellerbach et al. | 260/239.3 D |
| 3,853,953 | 12/1974 | Hellerbach et al. | 260/470 |

*Primary Examiner*—Henry R. Jiles
*Assistant Examiner*—Robert T. Bond
*Attorney, Agent, or Firm*—Samuel L. Welt; George M. Gould; Frank P. Hoffman

[57] ABSTRACT

1,4-Benzodiazepin-2-ones bearing an acylamidoalkyl-substituent in the 1-position and methods for the preparation thereof are disclosed. These 1,4-benzodiazepin-2-ones exhibit sedative, anti-convulsant and muscle relaxant activity.

1 Claim, No Drawings

PROCESS FOR PREPARING ALKYL (N-PHENYLSULFONYLOXY) CARBAMATES

DATA ON RELATED U.S. APPLICATIONS

This application is a division of Ser. No. 373,070, filed June 25, 1973, now U.S. Pat. No. 3,853,953, which, in turn, is a division of application Ser. No. 111,731, filed Feb. 1, 1971, now U.S. Pat. No. 3,772,271.

DESCRIPTON OF THE INVENTION

The present invention is directed to 1,4-benzodiazepin-2-ones which exhibit sedative, anti-convulsant and muscle relaxant activity. More particularly, the present invention is concerned with 1-substituted-1,3-dihydro-2H-1,4-benzodiazepin-2-ones of the general formula

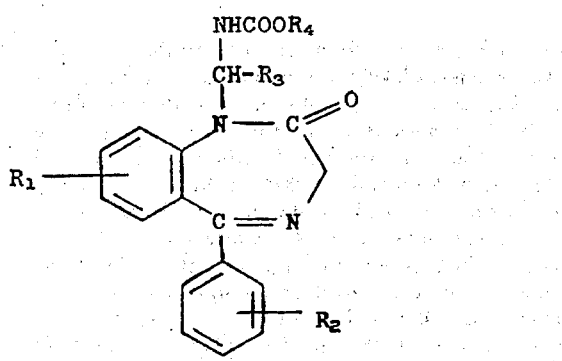

wherein $R_1$ signifies halogen or nitro; $R_2$ signifies hydrogen or halogen; $R_3$ signifies hydrogen, lower alkyl or aryl; $R_4$ signifies lower alkyl, and the pharmaceutically acceptable acid addition salts thereof.

As used herein, the term "lower alkyl" denotes straight or branched chain hydrocarbon groups containing from 1-7 carbon atoms, preferably 1-4 carbon atoms, such as methyl, ethyl, n-propyl, isopropyl, and the like. The expression "aryl" denotes a phenyl residue or a halo or lower alkyl-substituted phenyl residue such as o-tolyl, m-tolyl, p-tolyl, o-chlorophenyl, m-fluorophenyl, p-bromophenyl, and the like. The term "halogen" denotes all four forms thereof, i.e., fluorine, chlorine, bromine and iodine, unless indicated otherwise.

Among the preferred compounds falling within the scope of formula I above are those wherein the $R_1$ substituent is substituted at the 7-position of the benzodiazepine moiety. Likewise preferred are those compounds of formula I wherein $R_2$ is located in the ortho-position of the 5-phenyl ring if it represents halogen. Further preferred are the compounds of formula I wherein the $R_1$ substituent is chlorine or nitro and is located in the 7-position of the benzodiazepine moiety; the $R_2$ substituent is hydrogen, chlorine or fluorine and is located in the 2'-position of the benzodiazepine moiety, and the $R_3$ substituent is hydrogen, methyl or phenyl, i.e., compounds of the formula

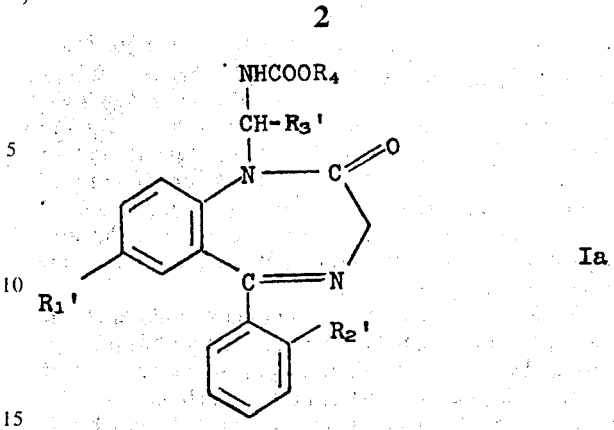

wherein
$R_4$ is as above;
$R_1'$ signifies chlorine or nitro;
$R_2'$ signifies hydrogen, chlorine or fluorine;
$R_3'$ signifies hydrogen, methyl or phenyl and the pharmaceutically acceptable acid addition salts thereof.

Most preferred of the compounds of formula I above are:
Ethyl-[(2,3-dihydro-7-nitro-2-oxo-5-phenyl-1H-1,4-benzodiazepin-1-yl)methyl]carbamate;
Ethyl-[(7-chloro-2,3-dihydro-2-oxo-5-phenyl-1H-1,4-benzodiazepin-1-yl)methyl]carbamate;
Ethyl-{[7-chloro-5-(2-chlorophenyl)-2,3-dihydro-2-oxo-1H-1,4-benzodiazepin-1-yl]methyl}carbamate;
Ethyl-[α-(7-chloro-2,3-dihydro-2-oxo-5-phenyl-1H-1,3-benzodiazepin-1-yl)benzyl]carbamate;
Ethyl-[1-(7-chloro-2,3-dihydro-2-oxo-5-phenyl-1H-1,4-benzodiazepin-1-yl)ethyl]carbamate.

The novel compounds of formula I above can be prepared following a variety of procedures.

A. In one process aspect of the present invention, the compounds of formula I may be prepared by reacting a compound of the formula

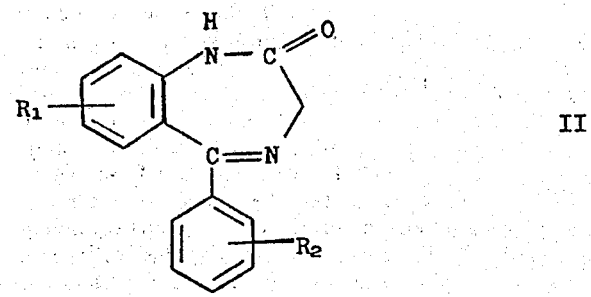

wherein $R_1$ and $R_2$ are as described above, with a compound of the formula

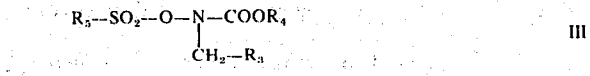

wherein $R_3$ and $R_4$ are as described above and $R_5$ signifies lower alkyl or aryl, in the presence of a base.

The reaction between the compounds of formulae II and III above is expediently effected in the presence of an anhydrous polar aprotic solvent such as dimethylformamide and like solvents. Preferred bases for the purposes of this process aspect include tertiary aliphatic amines such as triethylamine. Although temperature and pressure are not critical to this process aspect, it is preferable to effect the reaction at elevated temperatures, most preferably, at the reflux temperature of the reaction medium.

The $R_5$ substituent in the compounds of formula III can be, for example, methyl, ethyl, phenyl, p-bromophenyl, or p-tolyl. Examples of compounds of formula III suitable for the process include ethyl (N-methyl-N-p-toluenesulfonyloxy)carbamate, ethyl (N-benzyl-N-p-toluenesulfonyloxy)carbamate or ethyl (N-ethyl-N-p-toluenesulfonyloxy)carbamate.

The compounds of formula III above used as starting materials for this process aspect are new substances, and as such form a part of the present invention. These compounds of formula III can be prepared by acylating a compound of the general formula

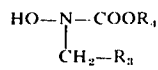

IV wherein $R_3$ and $R_4$ are as described above, with a reactive derivative of a sulfonic acid of the general formula

V wherein $R_5$ is as described above.

As reactive derivatives of the sulfonic acids of formula V, preferred are the halides, primarily the chlorides (such as p-toluenesulfonyl chloride). N-methyl-N-carbethoxyhydroxylamine, N-benzyl-N-carbethoxyhydroxylamine, N-ethyl-N-carbethoxyhydroxylamine, and the like is, for example, used as the compound of formula IV. The reaction conditions largely depend on the nature of the sulfonic acid derivative employed as the acylating agent. Thus, for example, the acylation is with advantage carried out in pyridine when an acid halide is used as the acylating agent.

The compounds of formula III above can be used not only for the purposes of this process aspect of the invention, but in addition as intermediates in many phases of preparative organic chemistry. For example, these compounds can be used generally for N-substitution of primary and secondary amides with the residue —CH($R_3$)—NH—COOR$_4$, wherein $R_3$ and $R_4$ are as described above. In reacting the compound of formula III with the amide to be substituted, the reaction is effected in the presence of a base. This reaction is expediently effected in the presence of an anhydrous polar aprotic solvent such as dimethylformamide and like solvents. Preferred bases for this purpose include tertiary aliphatic amines such as triethylamine. Although temperature and pressure are not critical to the successful performance of this reaction, it is preferable to effect the reaction at elevated temperatures, most preferably at the reflux temperature of the reaction medium.

The compounds of the above formula IV are known or are accessible according to known processes, for example, by reaction of the corresponding hydroxylamines of the formula

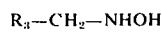

VI wherein $R_3$ is as described above, with a lower-alkyl ester of chloroformic acid.

B. In a second process aspect of the present invention, the compounds of formula I can be prepared by cyclizing a compound of the general formula

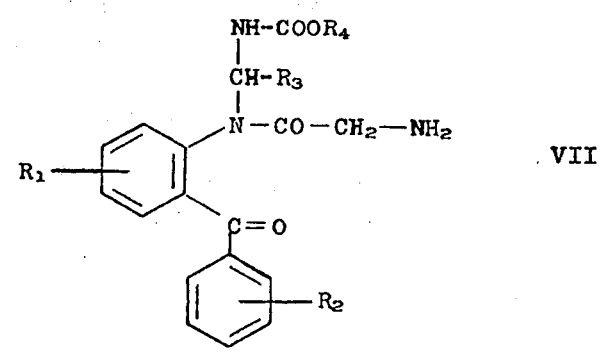

VII wherein $R_1$, $R_2$, $R_3$ and $R_4$ are as described above.

The cyclization of the compound of formula VII is readily effected in the presence of an inert organic solvent. Suitable solvents for this purpose include lower alkanols, such as methanol, ethanol, and the like, ethers such as dioxane, tetrahydrofuran, and the like, amides such as dimethylformamide, and the like. The cyclization reaction can also be effected in an aqueous medium. In a preferred embodiment of this process aspect, a solution, especially an aqueous solution of a suitable acid addition salt (i.e., the hydrochloride) of the compound of formula VII is made neutral to alkaline, for example, by addition of sodium carbonate solution, whereupon spontaneous cyclization to the corresponding derivative of formula I is effected.

Examples of compounds of formula VII suitable for this process aspect include 2-amino-N-[(ethoxycarbonylamino)methyl]-2'-benzoyl-4'-chloroacetanilide, 2-amino-N-[(ethoxycarbonylamino)methyl]-2'-benzoyl-4'-nitroacetanilide, 2-amino-N-[(ethoxycarbonylamino)methyl]-4'-chloro-2'-(o-chlorobenzoyl)-acetanilide, 2-amino-N-[α-(ethoxycarbonylamino)benzyl]-2'-benzoyl-4'-chloroacetanilide, 2-amino-N-[1-(ethoxycarbonylamino)ethyl]-2'-benzoyl-4'-chloroacetanilide and the like.

The compounds of formula VII above used as starting materials in this process aspect of the present invention can be prepared by reacting a compound of the formula

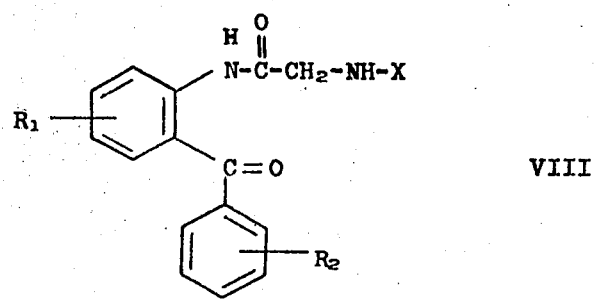

VIII wherein $R_1$ and $R_2$ are as described above, and X signifies any suitable protecting group, with a compound of formula III above in the presence of a base and subsequently splitting off the protecting group. A suitable protecting group for this purpose is a carbobenzoxy group which can be removed hydrogenolytically, for example, by hydrogen in the presence of a palladium catalyst. If the removal of the protecting group is effected in an acidic medium there results the acid addition derivative of the compound of formula VII. If removal of the protecting group is effected in neutral or alkaline medium, cyclization of the formula VII compound occurs spontaneously resulting in the corresponding compound of formula I.

The reaction between the compounds of formulae III and VIII is expediently effected in the presence of a base and an anhydrous polar aprotic solvent such as dimethylformamide and like solvents. Suitable bases for this purpose include tertiary aliphatic amines such as triethylamine. It is preferable to conduct this reaction at elevated temperatures, most preferably at the reflux temperature of the reaction medium.

The benzodiazepine derivatives of formula I are basic in nature and can be converted into their pharmaceutically acceptable acid addition salts by reaction with organic or inorganic acids. Examples of acids which form pharmaceutically acceptable salts are hydrogen chloride, hydrogen bromide, sulfuric acid, acetic acid, maleic acid, methanesulfonic acid, p-toluenesulfonic acid, and the like.

The compounds of formula I above exhibit sedative, anticonvulsant and muscle relaxant properties. The anti-convulsant activity of these compounds may be demonstrated by employing standard techniques. For example, the anti-convulsant activity can be shown by subjecting mice to which a compound of formula I or a salt thereof has been administered to the pentamethylene tetrazole test following the method disclosed by Orloff [Proc. Soc. Exptl. Biol. Med. 70, 254–257 (1949)]. The results are stated as "APR 2.0", which indicates that dosage (in mg/kg. p.o.) of an anti-convulsant which brings about double the pentamethylene tetrazole consumption compared with the untreated control group.

The muscle relaxant activity of the compounds of formula I can, for example, be demonstrated utilizing the rotating rod test. This test evaluates the ability of mice which are under the influence of a muscle relaxant or sedative compound to hold on to a slowly rotating rod. The rod used has a diameter of 30 mm. and rotates at a speed of two rotations per minute. For the test, those mice are selected which prior to receiving medication could hold on to the rotating rod for at least two minutes. After the mice are selected, these animals are given the compounds to be tested in various dosages. The animals are then placed on the rotating rod 30 minutes after administration of the compounds. The time for which each of the mice can stay on the rotating rod is calculated. The dosage which causes a 50 percent reduction of the time the animals hold on to the rod is designated as the $H.D._{50}$.

The toxicity of compounds of formula I is illustrated by the indication of the $L.D._{50}$.

The following table sets forth the results of the testing for representative compounds of formula I. These test reports relate to the following compounds:

I. Ethyl [(2,3-dihydro-7-nitro-2-oxo-5-phenyl-1H-1,4-benzodiazepin-1-yl)methyl]carbamate;

II. Ethyl [(7-chloro-2,3-dihydro-2-oxo-5-phenyl-1H-1,4-benzodiazepin-1-yl)methyl]carbamate;

III. Ethyl { [7-chloro-5-(2-chlorophenyl)-2,3-dihydro-2-oxo-1H-1,4-benzodiazepin-1-yl]-methyl}carbamate.

| Compound | Toxicity $(DI_{50})$ | Rotating Rod $(HD_{50})$ | Pentamethylene-tetrazole (APR 2.0) |
| --- | --- | --- | --- |
| I | 2500–5000 mg/kg. p.o. | 5 mg/kg. p.o. | 5.5 mg/kg. p.o. |
| II | 1250–2500 mg/kg. p.o. | 10 mg/kg. p.o. | 4 mg/kg. p.o. |
| III | > 5000 mg/kg. p.o. | 4 mg/kg. p.o. | 1 mg/kg. p.o. |

The compounds of formula I can be prepared in the form of various pharmaceutical preparations which contain them or their salts in admixture with a pharmaceutical, organic or inorganic inert carrier material which is suitable for enteral, percutaneous or parenteral application. Suitable carrier materials for this purpose include water, gelatin, gum arabic, lactose, starches, magnesium stearate, talc, vegetable oils, polyalkylene glycols, Vaseline, etc. The pharmaceutical formulations can be prepared in solid form (e.g., as tablets, dragees, suppositories, capsules); in semi-solid form (e.g., as ointments); or in liquid form (e.g., as solutions, suspensions or emulsions). They may be sterilized and/or contain additives such as preserving, stabilizing, wetting or emulsifying agents, salts for varying the osmotic pressure or buffers. They can also contain yet other therapeutically valuable substances. The dosage follows individual requirements, but a dosage of 0.1 mg/kg. to 5 mg/kg. per day is preferred.

The following Examples illustrate the invention. All temperatures are stated in degrees Centigrade.

EXAMPLE 1

A mixture of 14 g. of 1,3-dihydro-7-nitro-5-phenyl-2H-1,4-benzodiazepin-2-one, 20 g. of ethyl (N-methyl-N-p-toluene-sulphonyloxy)carbamate, 50 ml. of triethylamine and 50 ml. of dimethylformamide is boiled under reflux for 3 hours. The mixture is thereupon evaporated, initially in vacuum and then under high vacuum, and the residue is partitioned between methylene chloride and 10% sodium bicarbonate solution. The methylene chloride phase is separated off, washed with sodium carbonate solution and water, dried over sodium sulfate and evaporated. Chromatography of the residue on 500 g. of silica gel with 20% ethyl acetate in methylene chloride yields, after crystallization from methylene chloride-ether, ethyl [(2,3-dihydro-7-nitro-2-oxo-5-phenyl-1H-1,4-benzodiazepin-1-yl)methyl]-carbamate which melts at 157°–160° after recrystallization from methanol.

The ethyl (N-methyl-N-p-toluenesulphonyloxy)carbamate used as the starting material can be manufactured as follows:

A solution of 38 g. of p-toluenesulphonyl chloride in 100 ml. of pyridine is added dropwise with ice-cooling and constant stirring to a solution of 24 g. of N-methyl-N-carbethoxyhydroxylamine in 60 ml. of pyridine, in doing which the reaction temperature should not exceed 5°. The mixture is subsequently stirred for a further 4–5 hours at room temperature, the major part of the pyridine is removed on the rotary evaporator at a temperature of 50° and the residue is taken up with 100 ml. of water and 300 ml. of ether. The aqueous phase is separated off; the organic phase is washed 4 times with 60 ml. of hydrochloric acid each time until no more pyridine odor is to be perceived in the wash-water on treatment with alkali. The organic phase is washed with a further 80 ml. of sodium bicarbonate solution and subsequently dried over sodium sulfate. After removal of the ether, ethyl (N-methyl-N-*p*-toluenesulphonyloxy)carbamate remains as a readily mobile colorless oil which rapidly crystallizes. It is recrystallized from ether/petroleum ether and then melts at 46°–47°.

EXAMPLE 2

According to the procedure described in Example 1, from 2.7 g. of 7-chloro-1,3-dihydro-5-phenyl2H-1,4-benzodiazepin-2-one, 4.5 g. of ethyl (N-methyl-N-p-toluenesulphonyloxy)carbamate, 10 ml. of dimethylformamide and 20 ml. of triethylamine there is obtained, after chromatography on 150 g. of silica gel with 20% acetic ester in methylene chloride and crystallization from ether/hexane, ethyl [(7-chloro-2,3-dihydro-2-oxo-5-phenyl-1H-1,4-benzodiazepin-1-yl)methyl]carbamate which is recrystallized from methanol-water and then melts at 126°–129°.

EXAMPLE 3

In analogy to Example 1, by reaction of 6.1 g. of 7-chloro-5-(2-chlorophenyl)-1,3-dihydro-2H-1,4-benzodiazepin-2-one and 9 g. of ethyl (N-methyl-N-*p*-toluenesulphonyloxy)carbamate in 20 ml. of dimethylformamide and 40 ml. of triethylamine and crystallization from ethanol there is obtained ethyl {[7-chloro-5-(2-chlorophenyl)-2,3-dihydro-2-oxo-1H-1,4-benzodiazepin-1-yl] methyl}carbamate. This melts at 147°–149° after recrystallization from ethanol.

EXAMPLE 4

A mixture of 2 g. of 7-chloro-1,3-dihydro-5-phenyl-2H-1,4-benzodiazepin-2-one, 4 g. of ethyl (N-benzyl-N-p-toluenesulphonyloxy)carbamate, 10 ml. of dimethylformamide and 20 ml. of triethylamine is boiled under reflux for 4 hours. The mixture is subsequently evaporated and the residue partitioned between water and benzene. The benzene phase is washed with water, dried over sodium sulfate and evaporated. The crude product remaining as the residue is chromatographed on 150 g. of silica gel with 10% ethyl acetate in methylene chloride. The pure fractions crystallize from ether-hexane on standing in the refrigerator. After recrystallization from ethanol, there is obtained ethyl [α-(7-chloro-2,3-dihydro-2-oxo-5-phenyl-1H-1,4-benzodiazepin-1-yl(benzyl]carbamate of melting point 177°–170°.

The ethyl (N-benzyl-N-p-toluenesulphonyloxy)carbamate used as the starting product can be manufactured as follows:

31.9 g. of benzylhydroxylamine hydrochloride are treated with 130 ml. of 3N caustic soda, whereby the free base precipitates. This is dissolved in 50 ml. of chloroform and, with icecooling and powerful stirring, slowly treated dropwise at ca 5° with 21.6 g. of chloroformic acid ethyl ester. After completed addition, the ice-bath is removed and the mixture is further stirred at room temperature for a further 2 hours. The chloroform phase is thereafter separated off; the aqueous phase is saturated with sodium chloride and extracted with ether. The combined organic phases are dried over sodium sulfate. After evaporating off the solvent, N-benzyl-N-carbethoxyhydroxylamine remains as a pale orange-colored oil which is purified by distillation; boiling point 130°/0.05 mm Hg.

A solution of 19.5 g of the above N-benzyl-N-carbethoxy-hydroxylamine in 80 ml. of ether is underlayed with a solution of 5 g. of sodium hydroxide in 80 ml. of water. A solution of 19 g. of p-toluenesulphonyl chloride in 80 ml. of ether is thereupon slowly added dropwise with powerful stirring and with ice-cooling. After completed addition, the ice-bath is removed and the mixture is further stirred at room temperature for a further 2 hours. The two phases are then separated, the organic phase dried over sodium sulfate and the ether evaporated off. An orange oil remains which is dissolved in acetone and brought to crystallization at low temperature (ca −20°). The ethyl (N-benzyl-N-*p*-toluenesulphonyloxy)carbamate melts at 38°–40°.

EXAMPLE 5

A mixture of 10.8 g. of 7-chloro-1,3-dihydro-5-phenyl-2H-1,4-benzodiazepin-2-one, 20 g. of crude ethyl (N-ethyl-N-p-toluene-sulphonyloxy)carbamate, 40 ml. of dimethylformamide and 80 ml. of triethylamine is boiled under reflux for 4 hours. After evaporation in vacuum, the residue is partitioned between benzene and water. The benzene phase is washed with water, dried over sodium sulfate and evaporated. Crystallization of the residue from methylene chloride/ether gives back the unreacted starting material. The mother liquor is evaporated. By chromatography of the residue on 250 g. of silica gel with 20% ethyl acetate in methylene chloride, there is obtained, after crystallization from ethanol, pure ethyl [1-(7-chloro-2,3-dihydro-2-oxo-5-phenyl-1H-1,4-benzodiazepin-1-yl)ethyl]carbamate of melting point 155°–157°.

The ethyl (N-ethyl-N-p-toluenesulphonyloxy)carbamate used as the starting product is manufactured in accordance with the data in Examples 1 and 4 from N-ethyl-N-carbethoxyhydroxylamine and p-toluenesulphonyl chloride and is further processed as the crude product without prior purification.

EXAMPLE 6

An aqueous solution of 1 g. of 2-amino-N-[(ethoxycarbonylamino)methyl]-2'-benzoyl-4'-chloroacetanilide hydrochloride is made alkaline with 10% sodium carbonate solution. The base precipitated is extracted with methylene chloride. The extracts are dried over sodium sulfate and evaporated. The residue is taken up in ethanol and the solution obtained is boiled under reflux for 10 minutes. The crude product which remains as the residue after evaporation of the solution is crystallized from methanol/water. Ethyl [(7-chloro-2,3-dihydro-2-oxo-5-phenyl-1H-1,4-benzodiazepin-1-yl)methyl]carbamate of melting point 124°–216° is obtained.

The 2-amino-N-[(ethoxycarbonylamino)methyl]-2'-benzoyl-4'-chloroacetanilide hydrochloride used as the starting product can be manufactured as follows:

8.4 g of 2'-benzoyl-2-benzyloxycarbonylamino-4'-chloro-acetanilide and 9 g of ethyl (N-methyl-N-p-toluenesulphonyloxy) carbamate are boilded under reflux for 3 hours in a mixture of 20 ml of dimethylformamide and 40 ml of triethylamine. The reaction mixture is concentrated and then partitioned between water and ether. The ether phase is washed with water, dried over sodium sulphate and evaporated. Chromatography of the residue on 200 g of silica gel with 20% ethyl acetate in methylene chloride yields, besides unreacted starting material, pure N-[(ethoxycarbonylamino)methyl]-2'-benzoyl-2-benzyloxycarbonylamino-4'-chloroacetanilide as a colorless resin.

2.1 g of the above N-[(ethoxycarbonylamino)methyl]-2'-benzoyl-2-benzyloxycarbonylamino-4'-chloroacetanilide are hydrogenated for 45 minutes in 30 ml of ethanol in the presence of 0.5 g of palladium catalyst (5% on charcoal) and 5 mmol of hydrogen chloride. The mixture is thereupon filtered off the catalyst and concentrated in vacuum at 20°–30°. 2-Amino-N-[(ethoxycarbonylamino)methyl]-2'-benzoyl-4'-chloroacetanilide hydrochloride precipitates as a resin on treatment of the residue with ether. The solvent is decanted off and the residue stirred up with ether. The amorphous powder which is obtained on filtering off by suction is washed with ether and dried in vacuum. There is obtained an almost colorless product, the aqueous solution of which displays a pH of ca 4–5.

EXAMPLE 7

The following compounds can also be manufactured according to the process described in Example 6:

ethyl [(2,3-dihydro-7-nitro-2-oxo-5-phenyl-1H-1,4-benzodiazepin-1-yl)methyl]carbamate, melting point 157°–160° after crystallization from methanol (from 2-amino-N-[(ethoxycarbonylamino)methyl]-2'-benzoyl-4'-nitroacetanilide hydrochloride);

ethyl { [7-chloro-5-(2-chlorophenyl)-2,3-dihydro-2-oxo-1H-1,4-benzodiazepin-1-yl]methyl}carbamate, melting point 147°–149° after crystallization from ethanol (from 2-amino-N-[(ethoxycarbonylamino)methyl]-4'-chloro-2'-(o-chlorobenzoyl)acetanilide hydrochloride);

ethyl [α-(7-chloro-2,3-dihydro-2-oxo-5-phenyl-1H-1,4-benzodiazepin-1-yl)benzyl]carbamate, melting point 177°–179° after crystallization from ethanol (from 2-amino-N-[α-(ethoxy-carbonylamino)benzyl]-2'-benzoyl-4'-chloroacetanilide hydrochloride;

ethyl [1-(7-chloro-2,3-dihydro-2-oxo-5-phenyl-1H-1,4-benzodiazepin-1-yl)ethyl]carbamate, melting point 155°–157° after crystallization from ethanol (from 2-amino-N-[1-ethoxycarbonylamino)ethyl]-2'-benzoyl-4'-chloroacetanilide hydrochloride).

EXAMPLE 8

Tablets of the following composition are manufactured:

| | per tablet |
|---|---|
| Ethyl [(2,3-dihydro-7-nitro-2-oxo-5-phenyl-1H-1,4-benzodiazepin-1-yl)methyl]carbamate | 10 mg |
| Corn starch | 53 mg |
| Lactose | 150 mg |
| Gelatin (10% solution) | 6 mg |

The active substance, the corn starch and the lactose are mixed with a 10% gelatin solution. The paste is comminuted and the granulate dried in a suitable pan at 43°. The dried granulate is conducted through a comminuting machine and mixed with the following ingredients in a mixer:

| Talc | 6 mg |
|---|---|
| Magnesium stearate | 6 mg |
| Corn starch | 9 mg |

The mixture is thereupon compressed to tablets of 450 mg.

EXAMPLE 9

Suppositories are manufactured with the following ingredients:

| | per 1.3 g suppository |
|---|---|
| Ethyl [(2,3-dihydro-7-nitro-2-oxo-5-phenyl-1H-1,4-benzodiazepin-1-yl)methyl]carbamate | 0.025 g |
| Cocoa butter (melting point 36–37°) | 1.230 g |
| Carnauba wax | 0.045 g |

Cocoa butter and carnauba wax are melted, well mixed and cooled to 45°. The well comminuted active ingredient is thereupon added and stirred until distribution is complete and uniform. The mixture is poured into suppository moulds which ensure a suppository weight of 1.3 g. After cooling, the suppositories are taken from the moulds and indvidually wrapped in wax paper or metal foil.

EXAMPLE 10

A parenteral formulation is manufactured with the following ingredients:

| | per ml. |
|---|---|
| Ethyl [(2,3-dihydro-7-nitro-2-oxo-5-phenyl-1H-1,4-benzodiazepin-1-yl)methyl]carbamate | 5 mg. |
| Dimethylacetamide | 10% |
| Propylene glycol | 50% |
| Benzyl alcohol | 1.5% |
| Ethanol | 10% |
| Water for injection q.s. ad | 1 ml |

The active substance is dissolved in the dimethylacetamide, benzyl alcohol, propylene glycol, ethanol and water are added, the mixture is filtered through a candle filter and the filtrate is filled into ampules of a suitable size. The ampules are thereupon sealed and sterilized.

EXAMPLE 11

Tablets and suppositories and a parenteral formulation are manufactured according to the processes described in Examples 8 to 10, but ethyl [(7-chloro-2,3-dihydro-2-oxo-5-phenyl-1H-1,4-benzodiazepin-1-yl)methyl]carbamate or ethyl { [7-chloro-5-(2-chlorophenyl)2,3-dihydro-2-oxo-1H-1,4-benzodiazepin-1-yl]methyl}carbamate is used as the active substance.

We claim:

1. A process for preparing a compound of the formula:

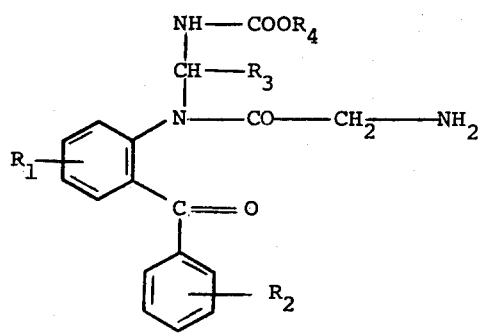

wherein
- $R_1$ signifies halogen or nitro;
- $R_2$ signifies hydrogen or halogen;
- $R_3$ signifies hydrogen, lower alkyl or aryl and
- $R_4$ signifies lower alkyl which comprises reacting a compound of the formula

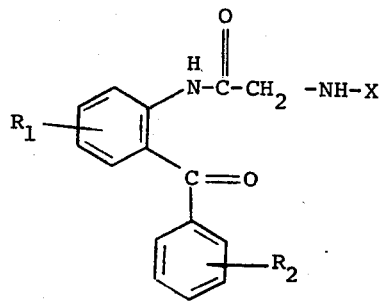

wherein $R_1$ and $R_2$ are as described above, and X signifies a carbobenzoxy group with a compound of the formula

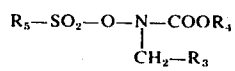

wherein $R_3$ and $R_4$ are as described above and $R_5$ signifies lower alkyl or a phenyl residue or a halo or lower alkyl-substituted phenyl residue, in the presence of a base and subsequently splitting off the carbobenzoxy group.

* * * * *